United States Patent
Ohno et al.

(10) Patent No.: US 7,722,857 B2
(45) Date of Patent: May 25, 2010

(54) IMMUNOADJUVANT

(75) Inventors: Tadao Ohno, Ibaraki (JP); Eiji Uchimura, Chiba (JP)

(73) Assignee: Cell-Medicine, Inc., Ibaraki (JP)

( * ) Notice: Subject to any disclaimer, the term of this patent is extended or adjusted under 35 U.S.C. 154(b) by 39 days.

(21) Appl. No.: 12/159,907

(22) PCT Filed: Jan. 6, 2006

(86) PCT No.: PCT/JP2006/300083

§ 371 (c)(1),
(2), (4) Date: Oct. 7, 2008

(87) PCT Pub. No.: WO2007/077629

PCT Pub. Date: Jul. 12, 2007

(65) Prior Publication Data

US 2009/0274763 A1   Nov. 5, 2009

(51) Int. Cl.
A61K 39/02 (2006.01)
A61K 39/38 (2006.01)
A61K 47/00 (2006.01)
A61K 51/00 (2006.01)

(52) U.S. Cl. ............... 424/1.61; 424/184.1; 424/234.1; 424/278.1

(58) Field of Classification Search .......... None
See application file for complete search history.

(56) References Cited

U.S. PATENT DOCUMENTS

| | | | |
|---|---|---|---|
| 5,759,582 A | 6/1998 | Leong et al. | |
| 7,247,310 B1 | 7/2007 | Ohno et al. | |
| 2003/0082232 A1 | 5/2003 | Lee et al. | |
| 2006/0008478 A1 | 1/2006 | Ohno et al. | |

FOREIGN PATENT DOCUMENTS

| | | |
|---|---|---|
| EP | 1 495 767 | 1/2005 |
| JP | 2002-524491 | 8/2002 |
| JP | 2003-306444 | 10/2003 |
| JP | 2005-126335 | 5/2005 |
| WO | 00/47226 | 8/2000 |
| WO | 03/028656 | 4/2003 |
| WO | 03/074079 | 9/2003 |

OTHER PUBLICATIONS

Dendritic Cells, Second Edition, pp. xviii-xxii, ed. Lotze, M.T. and Thomson, A.W., Academic Press, San Diego, 2001.
Geiger et al., "Vaccination of Pediatric Solid Tumor Patients with Tumor Lysate-pulsed Dendritic Cells Can Expand Specific T Cells and Mediate Tumor Regression" *Cancer Research* 61:8513-19, 2001.
English language abstract of JP 2003-306444, provided by Patent Abstracts of Japan, Oct. 28, 2003.
English Language abstract of JP 2005-126335 provided by Patent Abstracts of Japan, May 19, 2005.
Rhee et al., "Biomimetic configurational arrays of hydroxyapatite nanocrystals on bio-organics" *Biomaterials* 22(21):2843-47, 2001.
Burgos et al., "Controlled release of rhodium (II) carboxylates and their association complexes with cyclodextrins from hydroxyapatite matrix" *Biomaterials* 23:2519-26, 2002.
Kurosaka et al., "Production of Proinflammatory Cytokines by Phorbol Myristate Acetate-Treated THP-1 Cells and Monocyte-Derived Macrophages After Phagocytosis of Apoptotic CTLL-2 Cells" *J. Immunol.* 161:6245-49, 1998.
Hu et al., "*Escherichia coli* Expressing Recombinant Antigen and Listeriolysin O Stimulate Class I-Restricted CD8$^+$ T Cells following Uptake by Human APC" *J. Immunol.* 172:1595-1601, 2004.
Brett et al., "Comparison of Antigen Presentation of Influenza A Nucleoprotein Expressed in Attenuated AroA$^-$ *Salmonella typhimurium* with That of Live Virus" *J. Immunol.* 150:2869-2884, 1993.
He et al., "Calcium Phosphate Nanoparticle Adjuvant" *Clinical and Diagnostic Laboratory Immunology* 7(6):899-903, 2000.

*Primary Examiner*—Mark Navarro
(74) *Attorney, Agent, or Firm*—Greenblum & Bernstein, P.L.C.

(57) ABSTRACT

An immunoadjuvant comprising one kind or two or more kinds of immunostimulating substances carried separately by two or more kinds of different microparticle immunostimulating substance carriers, and comprising at least a combination of (a) an inorganic substance such as microparticle calcium phosphate having a size phagocytizable by cells, and (b) precipitates of a soluble protein and a mucopolysaccharide formed by coacervation as the microparticle immunostimulating substance carriers, which is highly safe and can exhibit potent immunoadjuvant activity.

16 Claims, 1 Drawing Sheet

IMMUNOADJUVANT

TECHNICAL FIELD

The present invention relates to an immunoadjuvant.

BACKGROUND ART

Most of immunoadjuvants widely used so far have two kinds of roles at a local administration site in vivo, specifically, (1) gradually releasing antigens to efficiently supply them to immunocompetent cells with maintaining the antigens in a state of aqueous or oil emulsion to prevent rapid disperse of the antigens, and (2) inducing inflammatory reactions and activating the immunocompetent cells gathering at the local inflammation site. In recent years, it has been revealed that antigen-presenting cells play a major role of immune responses in both of the humoral immune responses inducing antibody production and the cell-mediated immune responses inducing killer T cells, and that dendritic cells, macrophages, and B cells exist as the antigen-presenting cells. Among them, the dendritic cells have the most potent antigen-presenting ability (Dendritic Cells, Second edition, ed. by Lotze, M. T. and Thomson, A. W., Academic Press, San Diego, 2001). When a substance that can effectively activate antigen-presenting cells is administered to a living body together with an antigen, the substance acts as an immunoadjuvant and can efficiently induce and enhance immune responses against the antigen in both of the humoral immune responses and cell-mediated immune responses.

Among the variety of conventionally known immunoadjuvants, only a few immunoadjuvants are safe enough to be usable in a tumor immunotherapy for a purpose of therapeutic treatment, and prevention of metastasis and recurrence of human tumors, and also are inexpensive. For example, keyhole limpet hemocianin (KLH) has been used as an immunoadjuvant in a tumor immunotherapy by using cultured dendritic cells (Geiger, J. D., et al., Cancer Res., 61:8513-8519, 2001). However, this substance is expensive. Methods of directly administering cytokines such as granulocyte-macrophage colony stimulating factor (henceforth also abbreviated as "GM-CSF"), which directly activate dendritic cells, as immunoadjuvants have also been proposed. However, cytokines are still much more expensive.

As safe and inexpensive immunoadjuvants for manufacture of vaccines as a measure against infectious diseases, immunoadjuvants having insufficient activity such as alum (aluminum hydroxide), Freund's incomplete adjuvant (since this adjuvant is oily substance, toxicity is concerned), and Montanide have been used. Although these substances are less toxic compared with Freund's complete adjuvant (henceforth also abbreviated as "FCA") and Ribi adjuvant system, which are used in animal experiments, immunoadjuvant activities thereof are also weak.

Tuberculin for detection of *Mycobacterium tuberculosis* infection history, especially, tuberculin purified protein derivative (henceforth also abbreviated as "PPD"), which consists of protein ingredients in tuberculin purified by ammonium sulfate precipitation, is extremely safe even if repetitively administered to humans and moreover inexpensive. Therefore, tuberculin has been widespread all over the world. The inventors of the present invention found that PPD could be used as an immunoadjuvant (PCT/JP00/00692). The inventors of the present invention also found that, when PPD was formed as precipitate by coacervation with soluble proteins and mucopolysaccharides and then administered into tumor tissues denatured by a physical means, the PPD could served as an effective immunoadjuvant for inducing antitumor immune responses (Japanese Patent No. 3492671). This immunoadjuvant has a higher immunoadjuvant activity compared with dissolved PPD, and has extremely high safety in the same manner as the dissolved PPD. However, the immunoadjuvant activity thereof is insufficient if compared with lipopolysaccharides (henceforth also abbreviated as "LPS") which are major ingredients of FCA or endotoxins.

In peripheral blood, immature antigen-presenting cells flow which can phagocytize microparticle antigens. It is known that when a lipopolysaccharide (LPS) is added to cultured immature antigen-presenting cells in vitro, maturation of the cells is advanced to exhibit potent ability to present antigens. The antigen-presenting cells activated in this process release various kinds of cytokines, such as GM-CSF, interleukin (henceforth also abbreviated as "IL") 12, and interferon-γ (henceforth also abbreviated as "IFNg"). GM-CSF itself is essential as a cell growth factor of the dendritic cells. Therefore, the dendritic cells once activated become possible to maintain the activated state for a long period of time and continue to survive on the basis of the autocline mechanism of GM-CSF. Macrophages, as well as dendritic cells, are isogenic antigen-presenting cells which are differentiated from the same hematopoietic stem cells, and produce cytokines such as GM-CSF upon receipt of immunostimulation in the same manner as dendritic cell.

Practically, antitumor immune responses to tumor cells can be efficiently induced by administering solidified and microparticulated antigen tumor tissues as an antigen into a living body together with a cytokine such as GM-CSF (PCT/JP00/00692). This fact indicates that GM-CSF itself serves as an immunoadjuvant, and at the same time, an amount of GM-CSF produced from antigen-presenting cells stimulated with the immunoadjuvant can serve as an index representing the activity of the original immunoadjuvant. In other words, quantification of GM-CSF produced by antigen-presenting cells derived from a human enables successful estimation of immunoadjuvant activity in human in an in vitro experimental system without using human individuals.

By using peripheral blood adherent cells including antigen-presenting cells derived from human peripheral blood, the inventors of the present invention demonstrated, on the basis of the aforementioned means, that a potent immunoadjuvant action could be obtained by immobilizing soluble ingredients derived from microorganisms [soluble ingredients extracted with an organic solvent such as *Mycobacterium bovis Bacillus* Calmette-Guerin (henceforth also abbreviated as "BCG bacterium")] on a solidified tissue as an immunostimulating substance carrier (WO2003/074079).

The solidified tissue used as the immunostimulating substance carrier in the aforementioned immunoadjuvant is a biodegradable material which is digested in phagocytes including antigen-presenting cells and disappears without remaining in the body. However, when this immunoadjuvant is applied to a human individual, if a tissue used is not from the individual himself wherein major histocompatibility antigen is completely identical, or a tissue of the other one of monozygotic twins wherein major histocompatibility antigen is genetically identical, the immunostimulating substance carrier may have antigenicity to the human individual, and may sometimes induce an antigen-antibody reaction against the immunostimulating substance carrier or digested protein fragments thereof. This causes a problem that, when the aforementioned immunoadjuvant is used as a general-purpose immunoadjuvant (when a desired antigen is added to the immunoadjuvant to induce an immune response to the antigen), undesired antigen-antibody reactions against the immunostimulating substance carrier itself are induced, and the immune response to the antigen is buried among the whole immune responses and become unlikely to be manifested.

The inventors of the present invention also proposed a method for preparing calcium phosphate microparticles carrying one kind or two or more kinds of molecules to be carried (Japanese Patent Unexamined Publication (KOKAI) No. 2005-126335). These calcium phosphate microparticles consist of hydroxyapatite having a Ca/P molar ratio of 1.3 or higher. It has been further demonstrated that since amorphous calcium phosphate microparticles and low-crystalline apatite can carry not only hydrophilic protein molecules but also hydrophobic low molecules, they can serve as an immunostimulating substance carrier (Japanese Patent Unexamined Publication (KOHYO) No. 2002-524491). However, any immunoadjuvant consisting of a mixture of two or more kinds of immunostimulating substance carriers having completely different physicochemical properties and carrying one kind or two or more kinds of immunostimulating substances have not been known so far.

DISCLOSURE OF THE INVENTION

Object to be Achieved by the Invention

An object of the present invention is to provide an immunoadjuvant which has superior safety and can efficiently exhibit potent immunoadjuvant activity.

Means for Achieving the Object

The inventors of the present invention previously found that a high immunoadjuvant activity could be obtained by using tuberculin formulated as a sustained release preparation; that when tuberculin-proteins were mixed at the time of mixing albumin and heparin to form precipitates by coacervation, the tuberculin-proteins were caught into the precipitates to form insoluble microparticles that were served as the sustained release preparation; and that when these microparticles were administered in vivo together with soluble purified tuberculin as an immunoadjuvant with tumor cells as an antigen, they exhibited a potent tumor prophylactic effect, and when they were administered to a thermally denatured tumor tissue in vivo, they could induce a potent antitumor immune response (Japanese Patent No. 3492671).

It has also been demonstrated that calcium phosphate microparticles can serve as an immunostimulating substance carrier (Japanese Patent Unexamined Publication (KOHYO) No. 2002-524491), and the calcium phosphate microparticles produced by the method for producing calcium phosphate microparticles (Japanese Patent Unexamined Publication (KOKAI) No. 2005-126335) consist of hydroxyapatite having a Ca/P molar ratio of 1.3 or higher, contains a lot of nanometer size microparticles having a maximum diameter less than 1 μm, and are highly biocompatible and safe. An immunoadjuvant can be prepared by having PPD be carried on calcium phosphate microparticles as mentioned above with a size being capable of phagocytosed by antigen-presenting cells.

The inventors of the present invention conducted further researches to achieve the aforementioned object. As a result, they found that when soluble proteins contained in tuberculin, or soluble ingredients deriving from microorganisms or the like were used as immunostimulating substances, and said immunostimulating substance was made to be carried on each of (a) an inorganic substance and (b) precipitates formed by coacervation of a soluble protein and a mucopolysaccharide as a microparticle immunostimulating substance carrier, and then a mixture of the carriers was used as an immunoadjuvant, an extremely stronger synergistic immunoadjuvant action could be obtained compared with that obtained by solely using one kind of immunostimulating substance carrier. For example, it was found that when a mixture was used as an immunoadjuvant, which mixture comprised insoluble microparticles, obtained by mixing tuberculin-proteins in formation of precipitates from a mixture of albumin and heparin by coacervation, and comprised calcium phosphate microparticles, consisted of hydroxyapatite having a Ca/P molar ratio of 1.3 or higher obtainable according to the method described in Japanese Patent Unexamined Publication (KOKAI) No. 2005-126335 and made to carry PPD, a synergistically higher immunoadjuvant action could be obtained, which action markedly exceeded that of the immunoadjuvant activity obtainable by solely using each of the ingredients. The present invention was accomplished on the basis of these findings.

The present invention thus provides an immunoadjuvant comprising one kind or two or more kinds of immunostimulating substances carried by each of two or more kinds of different microparticle immunostimulating substance carriers, which at least comprises a combination of (a) an inorganic substance and (b) a precipitate of a soluble protein and a mucopolysaccharide formed by coacervation as said microparticle immunostimulating substance carriers.

According to a preferred embodiment of the present invention, there is provided the aforementioned immunoadjuvant, wherein the combination of two kinds of immunostimulating substance carriers consists of (a) calcium phosphate microparticle having a size phagocytizable by cells, and (b) precipitates of a soluble protein and a mucopolysaccharide formed by coacervation.

According to more preferred embodiments, there are provided the aforementioned immunoadjuvant, wherein the aforementioned calcium phosphate microparticle of (a) is calcium phosphate having a maximum diameter of 1 μm or smaller; and the aforementioned immunoadjuvant, wherein the aforementioned calcium phosphate microparticle of (a) is calcium phosphate microparticle having a Ca/P molar ratio of 1.3 or higher, containing 3 to 6% by weight of carbonate groups $CO_3^{2-}$, and having a degree of crystallinity, in an XRD spectrum obtained with a CuK α ray, not lower than a degree of crystallinity defined by appearance of broad peaks having centers at 2 θ values of 26°, 32° and 34° and appearance of a shoulder with a Miller index of 300 at 33°, and not higher than a degree of crystallinity defined by appearance of peaks or shoulders having centers at 26°, 28.1°, 29°, 32°, 33° and 34° and by separation of peaks with Miller indexes of 211 and 112.

According to other more preferred embodiments, there are provided the aforementioned immunoadjuvant, wherein the aforementioned soluble protein in (b) is albumin; the aforementioned immunoadjuvant, wherein the aforementioned mucopolysaccharide in (b) is heparin; and the aforementioned immunoadjuvant, wherein the aforementioned precipitates of a soluble protein and a mucopolysaccharide formed by coacervation of (b) are precipitates crosslinked by using an inter-protein molecule crosslinking agent.

There are further provided the aforementioned immunoadjuvant, wherein the immunostimulating substance consists of one kind or two or more kinds of immunostimulating substances selected from the group consisting of inducers of cytokines, chemokines, cell growth factors, and hormones; the aforementioned immunoadjuvant, wherein the immunostimulating substance consists of one kind or two or more kinds of immunostimulating substances selected from the group consisting of tuberculin, tuberculin purified protein derivative (PPD), soluble ingredients derived from microorganisms, trehalose 6,6'-dimycolate, LPS, lipid A, oligonucleotides, β-glucans, keyhole limpet hemocyanin, muramyl dipeptide, bestatin, levamisole, cytokines, chemokines, cell growth factors, and hormones; and the aforementioned immunoadjuvant, wherein the soluble ingredients derived from microorganisms consist of one kind or two or more kinds of extracts selected from the group consisting of alcohol extracts, acetone extracts, pyridine extracts, and hot water extracts of microorganisms.

From another aspect, there is provided the aforementioned immunoadjuvant, which is for internal administration to a mammal including human together with an antigen to induce a systemic immune response against the antigen.

According to a preferred embodiment of this invention, there is provided the aforementioned immunoadjuvant, wherein the antigen consists of one kind or two or more kinds of antigens selected from the group consisting of fungi, Actinomycetes, bacteria, viruses, phages, rickettsias, protozoans, ingredients of these microorganisms, tumor tissues, tumor cells, tumor cell ingredients, tumor antigen proteins, and tumor antigen peptides.

From a further aspect, there is provided the aforementioned immunoadjuvant, which is for administration into a tumor tissue of a mammal including human denatured by a physical means to induce an antitumor immune response.

According to a preferred embodiment of this invention, there is provided the aforementioned immunoadjuvant, wherein the physical means consists of one kind or two or more kinds of means selected from the group consisting of microwave irradiation, radiofrequency ablation, cryoablation, electrotome heating, hot water injection, alcohol injection, embolization, radiation exposure, laser beam irradiation and sonic disruption.

From a still further aspect, there is provided the aforementioned immunoadjuvant, which is for administration to a mammal including human after externally mixed with immunocompetent cells to induce a systemic immune response in the living body of the mammal.

According to a preferred embodiment of this invention, there is provided the aforementioned immunoadjuvant, wherein the immunocompetent cells consists of one kind or two or more kinds of cells selected from the group consisting of dendritic cells, macrophages, B lymphocytes, T lymphocytes, natural killer cells, natural killer T cells and hematopoietic stem cells.

There is further provided a vaccine containing the aforementioned immunoadjuvant and an antigen.

According to preferred embodiments of this invention, there are provided the aforementioned vaccine, wherein the antigen consists of one kind or two or more kinds of antigens selected from the group consisting of fungi, Actinomycetes, bacteria, viruses, phages, rickettsias, protozoans, and ingredients of these microorganisms, and which is for use in prophylactic and/or therapeutic treatment of an infectious disease; and the aforementioned vaccine, wherein the antigen consists of one kind or two or more kinds of antigens selected from the group consisting of tumor tissues, tumor cells, tumor cell ingredients, tumor antigen proteins, and tumor antigen peptides, and which is for use in prophylactic and/or therapeutic treatment of a tumor.

Further, by using, for example, a foreign protein as the antigen, antibodies directed to the antigen can be efficiently produced in a mammal other than human with the aforementioned immunoadjuvant. Therefore, an antibody-producing animal and an antibody-producing cell or antibody gene derived from the antibody-producing animal are provided by the present invention.

The present invention further provides a tumor vaccine comprising the aforementioned immunoadjuvant for administration into a tumor tissue of a mammal including human denatured by a physical means to induce an antitumor immune response; a tumor vaccine comprising the aforementioned immunoadjuvant for administration to a mammal including human after externally mixed with immunocompetent cells to induce an antitumor immune response in the living body of the mammal; and a tumor vaccine comprising the aforementioned immunoadjuvant for administration to a mammal including human after externally mixed with immunocompetent cells and an antigen to induce an antitumor immune response in the living body of the mammal.

From still further aspects, the present invention provides a method for inducing a systemic immune response, which comprises the step of administrating the aforementioned immunoadjuvant to a mammal including human; a method for inducing an antitumor immune response, which comprises the step of denaturing a tumor tissue of a mammal including human by a physical means and then administrating the aforementioned immunoadjuvant into the tumor tissue; and a method for inducing a systemic immune response, which comprises the step of externally mixing the aforementioned immunoadjuvant and immunocompetent cells beforehand and administering the mixture into a living body of a mammal including human.

BEST MODE FOR CARRYING OUT THE INVENTION

Figure 1:
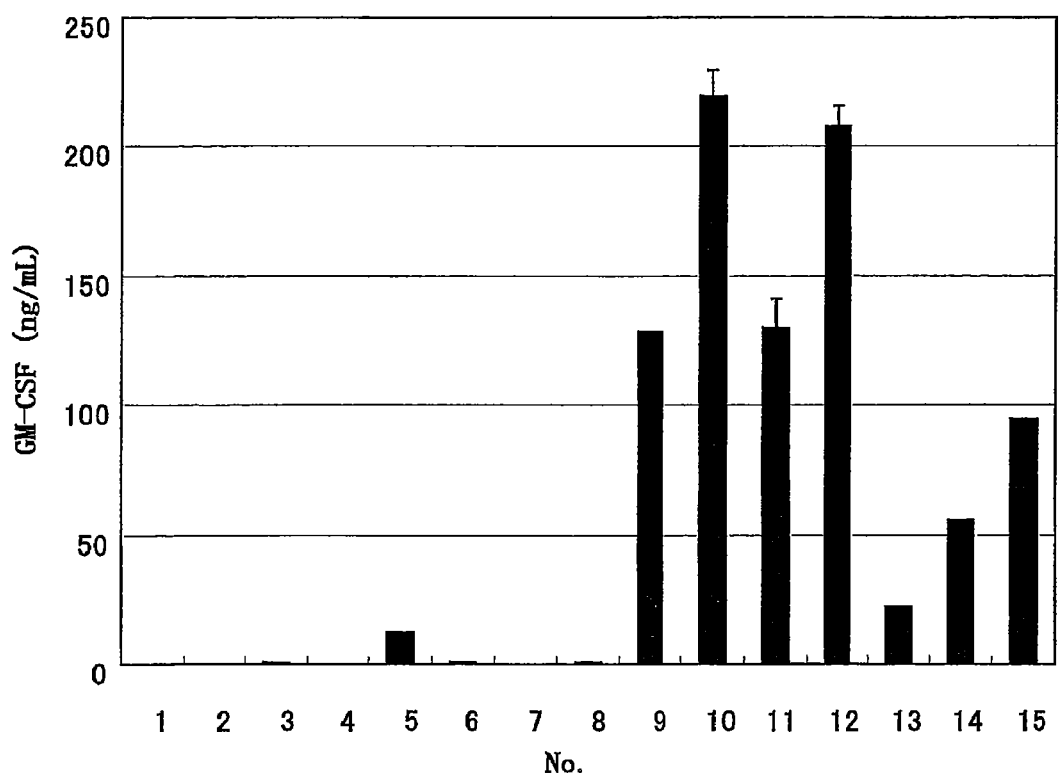
FIG. 1 shows the antigen-presenting cell-stimulating effect of the immunoadjuvant of the present invention in which two kinds of immunostimulating substances were carried separately on two kinds of different immunostimulating substance carriers. Calcium phosphate (henceforth also abbreviated as "CaP") was used as the carrier, and a BCG bacterium extract was carried as an immunostimulating substance. TuMP which carried PPD on coacervation precipitate microparticles as a carrier was used.

The meanings of the terms used in this specification are as follows.

The "immunostimulating substance" is a substance which internally induces and/or enhances a certain immune response in a mammal including human when administered to the mammal, and a substance which induces and/or enhances a certain kind of activation in antigen-presenting cells of a mammal including human when externally added to the cells. Therefore, an antigen itself is included in the immunostimulating substance so long as the antigen has a certain immunostimulating action.

The "immunostimulating substance carrier" is a substance for carrying the aforementioned immunostimulating substance. Although the immunostimulating substance carrier per se has no immunostimulating action or has an extremely low immunostimulating action in many cases, an immunostimulating substance carrier per se may sometimes have an immunostimulating action.

The "two or more kinds of different immunostimulating substance carriers" and synonyms thereof include two or more kinds of immunostimulating substance carriers consisting of different chemical substances or different compositions, as well as immunostimulating substance carriers consisting of the same chemical substance or composition but having different physicochemical properties. For example, two kinds of compositions comprising the same ingredients but in different ratios of the ingredients can be used as the two kinds of immunostimulating substance carriers. Further, microparticles consisting of the same chemical substance or composition and having different physicochemical properties of particle surfaces and the like also fall within the scope of the term. In this specification, the term should not be construed limitatively in any sense, and should be construed in broadest sense thereof.

The "immunoadjuvant" is a substance or composition which can induce and/or enhance an immune response against an antigen. Although an immunostimulating substance carrier which does not substantially have an immunostimulating action per se may be called as immunoadjuvant, an immunoadjuvant in general often means a combination of the carrier and a certain immunostimulating substance. Further, an immunostimulating substance per se may also be called as immunoadjuvant. The immunoadjuvant of the present invention means one kind or two or more kinds of immunostimulating substances carried separately by two or more kinds of immunostimulating substance carriers, and the immunoadjuvant essentially includes a combination of an immunostimulating substance carrier and an immunostimulating substance.

The immunoadjuvant of the present invention is characterized in that it comprises one kind or two or more kinds of immunostimulating substances carried separately by two or more kinds of different microparticle immunostimulating substance carriers, wherein at least one of the microparticle immunostimulating substance carriers consists of an inorganic substance, and the other consists of precipitates of a soluble protein and a mucopolysaccharide formed by coacervation. The immunoadjuvant of the present invention comprises a combination of (a) an inorganic substance and (b) precipitates of a soluble protein and a mucopolysaccharide formed by coacervation as the microparticle immunostimulating substance carriers, and the same or different immunostimulating substances are carried by each of the microparticle immunostimulating substance carriers of (a) and (b). One kind of immunostimulating substance may be used, or two or more kinds of substances may also be used. For example, typically, each of the microparticle immunostimulating substance carriers of (a) and (b) mentioned above may carry each one different kind of immunostimulating substances, or each of the microparticle immunostimulating substance carriers of (a) and (b) may carry the same kind of immunostimulating substance. Alternatively, one of the microparticle immunostimulating substance carriers of (a) and (b) mentioned above may carry two different kinds of immunostimulating substances, and the other immunostimulating substance carrier may carry one kind or both kinds of the immunostimulating substances.

Each of the microparticle immunostimulating substance carriers of (a) and (b) mentioned above may consist of two or more kinds of microparticle immunostimulating substance carriers comprising different chemical substances or different compositions, or each of them may consist of a mixture of microparticle immunostimulating substance carriers comprising the same chemical substance or composition but having different physicochemical properties. For example, as the above microparticle immunostimulating substance carrier of (b) which consists of precipitates, a mixture of two kinds of compositions consisting of a combination of the same ingredients in different ratios of the ingredients may be used.

Alternatively, as the above microparticle immunostimulating substance carrier of (a) which consists of an inorganic substance, a mixture of microparticles consisting of the same inorganic substance but having different physicochemical properties of particle surfaces may be used.

Although the immunoadjuvant of the present invention comprises a combination of the immunostimulating substance carriers of (a) and (b) mentioned above each carrying the immunostimulating substance, it may further contain an immunostimulating substance carrier not carrying any immunostimulating substance. In such a case, it is desirable to choose an immunostimulating substance carrier which per se has an immunostimulating action as the immunostimulating substance carrier. Moreover, the immunoadjuvant of the present invention may further contain an immunostimulating substance not carried by an immunostimulating substance carrier.

In a preferred embodiment, as the combination of two kinds of immunostimulating substance carriers, (a) microparticle calcium phosphate having a size phagocytizable by cells, and (b) precipitates of a soluble protein and a mucopolysaccharide formed by coacervation are included. Although this specific embodiment will be explained in detail below, the immunoadjuvant of the present invention is not limited to this specific embodiment. The combination of (a) microparticle calcium phosphate having a size phagocytizable by cells, and (b) precipitates of a soluble protein and a mucopolysaccharide formed by coacervation is not particularly limited, and types, ratios, preparation methods, and the like of those ingredients may be arbitrarily chosen. A third ingredient may be mixed in the immunoadjuvant of the aforementioned embodiment. As the third ingredient, besides an antigen, an immunostimulating substance different from the carried immunostimulating substance and the like may be used. The antigen may be carried by a solid carrier, and as the carrier, the aforementioned microparticle immunostimulating substance carrier of (a) or (b) mentioned above may be used. The immunoadjuvant of the present invention may contain the same immunostimulating substance as the immunostimulating substance carried by the ingredient (a) or (b) in a state that it is not carried by a carrier.

The microparticles of calcium phosphate having a size phagocytizable by cells can be prepared by using, for example, the method described in Japanese Patent Unexamined Publication (KOKAI) No. 2005-126335. As the microparticles of calcium phosphate, any kinds of microparticle calcium phosphate can be used. For example, those obtained by grinding commercially available calcium phosphate by a method well known to those skilled in the art, and selecting microparticle calcium phosphate having a size phagocytizable by cells may be used, or those prepared from a phosphoric acid solution and a calcium solution may also be used.

Further, those obtained by precipitating or depositing calcium phosphate on microparticle base materials to form coatings of calcium phosphate on the surfaces of the base materials may also be used. Such embodiment also falls within the scope of the microparticle calcium phosphate. The base materials are not particularly limited so long as they are microparticles having a size phagocytizable by cells. For example, collagen as a fibrous protein insoluble in a neutral region or chondroitin sulfate which is a water-soluble sugar chain polymer can be coprecipitated with low-crystalline apatite in the process of mixing a calcium hydroxide suspension and a phosphoric acid solution to prepare a collagen/chondroitin sulfate-apatite composite comprising fine crystals of nanometer size (Rhee, S. H., et al., Biomaterials., 22 (21), pp. 2843-2847, 2001), and such microparticles can also be used as the base materials. However, the base materials for the preparation of the microparticle calcium phosphate are not limited to these examples.

Type of calcium phosphate is not particularly limited, and may be any of anhydride, anhydrous salt, and hydrated salt, and may be a crystalline or amorphous substance. Furthermore, a part of calcium or a part of phosphoric acid may be replaced with other atoms or atomic groups. Specific examples of such calcium phosphate include, for example, apatite ($Ca_{10}(PO_4)_6(OH)_2$), calcium-deficient apatite, apatite in which metal ions substitute a part of Ca, apatite in which sulfate ions substitute a part of phosphate ions, amorphous calcium phosphate, amorphous calcium phosphate in which metal ions substitute a part of Ca, octacalcium phosphate ($Ca_8H_2(PO_4)_6 \cdot 5H_2O$), tricalcium phosphate ($Ca_3(PO_4)_2$), tricalcium phosphate in which metal ions substitute a part of Ca, and the like. However, calcium phosphate is not limited to these examples.

Preferably, calcium phosphate may be carbonic acid-containing calcium phosphate comprising 1 to 15% by weight of carbonate groups $CO_3^{2-}$. Type of the carbonic acid-containing calcium phosphate is not particularly limited, and may be any of anhydride, anhydrous salt, and hydrated salt, and may be a crystalline or amorphous substance. Example of the carbonic acid-containing calcium phosphate include carbonic acid-containing apatite, carbonic acid-containing amorphous calcium phosphate, and the like. The seat occupied by the carbonic acid group is not particularly limited, and may be, for example, the phosphate site or hydroxyl group site, or the so-called non-apatite site or surface adsorption site. Particularly preferred examples include microparticle calcium phosphate having a Ca/P molar ratio of 1.3 or higher, containing 3 to 6% by weight of carbonate groups $CO_3^{2-}$, and having a degree of crystallinity, in an XRD spectrum obtained with a CuK α ray, not lower than a degree of crystallinity defined by appearance of broad peaks having centers at 2 θ values of 26°, 32° and 34° and appearance of a shoulder with a Miller index of 300 at 33°, and not higher than a degree of crystallinity defined by appearance of peaks or shoulders having centers at 26°, 28.1°, 29°, 32°, 33° and 34° and by separation of peaks with Miller indexes of 211 and 112.

The size of the microparticles allowing phagocytosis thereof by cells is generally preferably 10 μm or smaller, most preferably 1 μm or smaller, in terms of the maximum diameter. Although human cells per se generally have a size of about 20 μm in diameter in the case of a spherical shape, adhering cells or gigantically grown cells without division for a long period of time may have a major axis exceeding 100 μm. Macrophages having a high phagocytic activity may phagocytize microparticles of 20 μm or larger in diameter. Therefore, the size phagocytizable by cells is not particularly limited.

As the method for using microparticle calcium phosphate having a size phagocytizable by cells as the immunostimulating substance and allowing an immunostimulating substance be carried thereon, the method described in, for example, Japanese Patent Unexamined Publication (KOKAI) No. 2005-126335 can be used. However, the method is not limited to this method. Among calcium phosphate materials, hydroxyapatite fine powder is used as an adsorbent for various substances, since it has a specific surface area as large as 100 $m^2$/g, and has superior adsorption ability. It is considered that hydroxyapatite fine powder can serve as a base material for preparing an adsorption type sustained-release medicament by using various compounds, and is suggested to have sustained-release property according to the diffusion model based on adsorption and desorption (Burgos, A. E., et al., Biomaterials., 23, pp. 2519-2526, 2002). In addition, it is known that calcium phosphate such as low-crystalline apatite and amorphous calcium phosphate can serve as a safe base material of a sustained-release medicament of a physiologically active biological substance such as proteins, since the material is originally a substance in a living body. Microparticles consisting of these apatites can also be used as the immunostimulating substance carrier.

Type of the immunostimulating substance to be carried by the microparticle calcium phosphate having a size phagocytizable by cells is not particularly limited. Since hydroxyapatite fine powder has superior adsorption ability as mentioned above, various substances can be used as the immunostimulating substance to be carried. As the immunostimulating substance, for example, one kind or two or more kinds of substances selected from the group consisting of inducers of cytokines, chemokines, cells growth factors, and hormones can be used, and it is preferable to use, for example, one kind or two or more kinds of substances selected from the group consisting of tuberculin, PPD, soluble ingredients originating in microorganisms, trehalose 6,6'-dimycolate, LPS, lipid A, oligonucleotides, β-glucans, keyhole limpet hemocyanin, muramyl dipeptide, bestatin, levamisole, cytokines, chemokines, cell growth factors, and hormones. As the soluble ingredients derived from microorganisms, for example, one kind or two or more kinds of extracts selected from the group consisting of alcohol extracts, acetone extract, pyridine extracts, and hot water extracts of microorganisms can be used. The inducers of cytokines, chemokines, cells growth factors, and hormones include bacterial cells and bacterial cell ingredients. However, the immunostimulating substance to be carried by calcium phosphate microparticles is not limited to these examples.

As the cytokines, chemokines, cells growth factors, and hormones, any substance which can stimulate antigen-presenting cells to induce cytokine production thereof may be used. Examples include, for example, interferon-α, interferon-β, interferon-γ, interleukins (ILs) (e.g., IL-1, IL-2, IL-3, IL-4, IL-7, IL-11, IL-12, IL-18, IL-27 etc.), colony stimulating factors (CSF) (e.g., G-CSF, GM-CSF, M-CSF etc.), epidermal growth factor (EGF), fibroblast growth factors (FGFs) (e.g., FGF-1, FGF-2, FGF-7 etc.), insulin, human growth hormone, and the like.

The method for extracting soluble ingredients derived from microorganisms with an organic solvent and/or hot water used in the step of preparing the soluble ingredients is not particularly limited, and methods well known to those skilled may be used. For example, it is preferable to prepare an extract by using ethanol. As the microorganisms usable in the step of preparing soluble ingredients originating in microorganisms, for example, bacteria, fungi, Actinomycetes and the like can be exemplified. Bacteria can be preferably used. Examples of more preferred bacteria are listed below. Any one kind of these bacteria may be used, or two or more kinds of these bacteria may be used in combination.

*Corynebacterium diphtheriae; Corynebacterium pseudotuberculosis; Corynebacterium xerosis; Corynebacterium renale; Corynebacterium kutscheri, Corynebacterium pseudodiphtheriticum; Corynebacterium equi; Corynebacterium bovis; Corynebacterium parvum; Corynebacterium paurometabolum; Corynebacterium pyogenes; Corynebacterium enzymicum; Corynebacterium hoagii; Corynebacterium striatum; Corynebacterium murisepticum; Corynebacterium nephridii; Corynebacterium phocae; Corynebacterium vaginalis; Microbacterium flavum; Corynebacterium fascians; Corynebacterium rathayi; Corynebacterium agropyri; Corynebacterium tritici;*

*Corynebacterium iranicum; Corynebacterium sepedonicum; Corynebacterium beticola; Corynebacterium ilicis; Corynebacterium humiferum; Corynebacterium humuli; Corynebacterium hypertrophicans; Corynebacterium acetoacidophilum; Corynebacterium acetophilum; Corynebacterium aurantiacum; Corynebacterium callunae; Corynebacterium citreum-mobilis; Corynebacterium ethanolaminophilum; Corynebacterium flaccumfaciens; Corynebacterium glutamicum; Corynebacterium herculis; Corynebacterium hydrocarboclastus; Corynebacterium lilium; Corynebacterium luteum; Corynebacterium mediolanum; Corynebacterium melassecola; Corynebacterium mycetoides; Corynebacterium nubilum; Corynebacterium roseum; Corynebacterium sanguinis; Arthrobacter globiformis; Arthrobacter simplex; Arthrobacter tumescens; Arthrobacter citreus; Arthrobacter terregens; Arthrobacter flavescens; Arthrobacter duodecadis; Arthrobacter luteus; Arthrobacter marinus; Arthrobacter variabilis; Arthrobacter viscosus; Arthrobacter polychromogenes; Arthrobacter consociatus; Arthrobacter nicotinovorus; Brevibacterium linens; Brevibacterium acetylicum; Brevibacterium erythrogenes; Brevibacterium healii; Brevibacterium lipolyticum; Brevibacterium brunneum; Brevibacterium fulvum; Brevibacterium fuscum; Brevibacterium helvolum; Brevibacterium immotum; Brevibacterium marinopiscum; Brevibacterium sociovivum; Brevibacterium stationis; Brevibacterium maris; Brevibacterium imperiale; Brevibacterium incertum; Brevibacterium insectiphilium; Brevibacterium minutiferula; Brevibacterium quale; Brevibacterium tegumenticola; Brevibacterium ammoniagenes; Brevibacterium sulfureum; Brevibacterium protophormiae; Brevibacterium saperdae; Brevibacterium flavum; Brevibacterium immariophilum; Brevibacterium lactofermentum; Brevibacterium roseum; Brevibacterium saccharolyticum; Brevibacterium divaricatum; Brevibacterium leucinophagum; Brevibacterium liquefaciens; Brevibacterium pentoso-alanicum; Brevibacterium pentoso-aminoacidicum; Brevibacterium lyticum; Brevibacterium albidum; Brevibacterium citreum; Brevibacterium luteum; Brevibacterium testaceum; Brevibacterium pusillum; Brevibacterium alanicum; Brevibacterium aminogenes; Brevibacterium chromogenes; Brevibacterium frigoritolerans; Brevibacterium halotolerans; Brevibacterium fermentans; Brevibacterium oxydans; Microbacterium lacticum; Microbacterium liquefaciens; Microbacterium flavum; Microbacterium thermosphactum; Cellulomonas flavigena; Cellulomonas acidula; Cellulomonas aurogena; Cellulomonas galba; Cellulomonas pusilla; Kurthia zopfii; Kurthia variabilis; Kurthia bessonii; Propionibacterium freudenreichii; Propionibacterium thoenii; Propionibacterium acidipropionici; Propionibacterium jensenii; Propionibacterium avidum; Propionibacterium acnes; Propionibacterium acnes* Type II, *Propionibacterium lymphophilum; Propionibacterium granulosum; Eucobacterium foedans; Eucobacterium alactolyticum; Eucobacterium rectale; Eucobacterium limosum; Eucobacterium ruminantium; Eucobacterium saburreum; Eucobacterium budayi; Eucobacterium nitritogenes; Eucobacterium ventriosum; Eucobacterium mutiforme; Eucobacterium cylindroids; Eucobacterium moniliforme; Eucobacterium tortuosum; Eucobacterium cellulosolvens; Eucobacterium combesii; Eucobacterium tenue; Eucobacterium fissicatena; Eucobacterium contortum; Eucobacterium aerofaciens; Eucobacterium lentum; Eucobacterium endocarditidis; Eucobacterium helminthoides; Eucobacterium pseudotortuosum; Eucobacterium obstii; Eucobacterium ethylicum; Eucobacterium helwigiae; Eucobacterium ureolyticum; Eucobacterium parvum; Actinomyces bovis; Actinomyces odontolyticus; Actinomyces israeli; Actinomyces naeslundii; Actinomyces viscosus; Actinomyces eriksonii; Actinomyces humiferus; Actinomyces suis; Arachnia propionica; Bifidobacterium bifidum; Bifidobacterium adolescentis; Bifidobacterium infantis; Bifidobacterium breve; Bifidobacterium longum; Bifidobacterium pseudolongum; Bifidobacterium thermophilum; Bifidobacterium suis; Bifidobacterium asteroids; Bifidobacterium indicum; Bifidobacterium coryneforme; Bacterionema matruchotii; Rothia dentocariosa; Mycobacterium tuberculosis; Mycobacterium microti; Mycobacterium bovis; Mycobacterium bovis BCG; Mycobacterium africanum; Mycobacterium kansasii, Mycobacterium marinum; Mycobacterium simiae; Mycobacterium gastri; Mycobacterium nonchromogenicum; Mycobacterium terrae; Mycobacterium triviale; Mycobacterium gordonae; Mycobacterium scrofulaceum; Mycobacterium paraffinicum; Mycobacterium intracellulare; Mycobacterium avium; Mycobacterium xenopi; Mycobacterium ulcerans; Mycobacterium phlei, Mycobacterium vaccae; Mycobacterium diernhoferi, Mycobacterium smegmatis; Mycobacterium thamnopheos; Mycobacterium flavescens; Mycobacterium fortuitum; Mycobacterium peregrinum; Mycobacterium chelonei; Mycobacterium paratuberculosis; Mycobacterium leprae; Mycobacterium lepraemurium; Frankia alni; Frankia elaeagni, Frankia discariae; Frankia ceanothi; Frankia coriariae; Frankia dryadis; Frankia purshiae; Frankia cercocarpi; Frankia brunchorstii; Frankia casuarinae; Actinoplanes philippinensis; Actinoplanes armeniacus; Actinoplanes missouriensis; Actinoplanes utahensis; Spirillospora albida; Streptosporangium roseum; Streptosporangium vulgare; Streptosporangium amethystogenes; Streptosporangium pseudovulgare; Streptosporangium nondiastaticum; Streptosporangium longisporum; Streptosporangium viridogriseum; Streptosporangium album; Streptosporangium albidum; Streptosporangium viridialbum; Streptosporangium rubrum; Amorphosphorangium auranticolor; Ampullariella regularis; Ampullariella campanulata; Ampullariella lobata; Ampullariella digitata; Pilimelia terevasa; Pilimelia anulata; Planomonospora parontospora; Planomonospora venezuelensis; Planobispora longispora; Planobispora rosea; Dactylosporangium aurantiacum; Dactylosporangium thailandense; Dermatophilus congolensis; Geodermatophilus obscurus; Nocardia farcinica; Nocardia otitidus-caviarum; Nocardia brasiliensis; Nocardia asteroids; Nocardia transvalensis; Nocardia formicae; Nocardia coeliaca; Nocardia polychromogenes; Nocardia paraffinae; Nocardia petroleophila; Nocardia saturnea; Nocardia kuroishii; Nocardia rugosa; Nocardia rhodnii; Nocardia vaccinii; Nocardia minima; Nocardia blackwellii; Nocardia convoluta; Nocardia cellulans; Nocardia lutea; Nocardia globerula; Nocardia rubropertincta; Nocardia corallina; Nocardia salmonicolor; Nocardia rubra; Nocardia opaca; Nocardia calcarea; Nocardia restricta; Nocardia erythropolis; Nocardia marina; Nocardia atlantica; Nocardia aerocolonigenes; Nocardia aurantia; Nocardia butanica; Nocardia dassonvillei; Nocardia histidans; Nocardia madurae; Nocardia neoopaca; Nocardia pellegrino; Nocardia pelletieri; Nocardia sylvodorifera; Nocardia turbata; Nocardia tenuis; Nocardia variabilis; Pseudonocardia thermophila; Pseudonocardia spinosa; Streptomyces albolongus; Streptomyces viridaris; Streptomyces albo-niger, Streptomyces albosporeus; Streptomyces albovinaceus; Streptomyces aureocirculatus; Streptomyces baarnensis; Streptomyces clavifer; Streptomyces galtieri; Streptomyces bobili; Streptomyces longispororuber; Streptomyces longisporus; Streptomyces herbeus; Streptomyces albofaciens; Streptomyces albus; Streptomyces albus* subsp. *bruneomycini; Streptomyces albus* subsp. *pathocidicus;*

*Streptomyces almquistii; Streptomyces aminophilus; Streptomyces cacaoi; Streptomyces chrestomyceticus; Streptomyces flocculus; Streptomyces gibsonii; Streptomyces herbescens; Streptomyces iodoformicus; Streptomyces ochraceiscleroticus; Streptomyces rangoon; Streptomyces rimosus; Streptomyces rimosus* subsp. *paromomycinus; Streptomyces rimosus* subsp. *pseudoverticillatus; Streptomyces spiroverticillatus; Streptomyces subflavus; Streptomyces varsoviensis; Streptomyces xantholiticus; Streptomyces albus* subsp. *fungatus; Streptomyces hydrogenans; Streptomyces vendargus; Streptomyces achromogenes; Streptomyces antibioticus; Streptomyces bikiniensis; Streptomyces cacaoi* subsp. *asoensis; Streptomyces cinereoruber; Streptomyces cinereoruber* subsp. *fructofermentans; Streptomyces cylindrosporus* subsp. *piceus; Streptomyces ederensis; Streptomyces fulvoviolaceus; Streptomyces fulvoviridis; Streptomyces gardneri; Streptomyces globosus; Streptomyces griseorubiginosus; Streptomyces herbaricolor; Streptomyces indigoferus; Streptomyces litmocidini; Streptomyces narbonensis; Streptomyces nashvillensis; Streptomyces noboritoensis; Streptomyces phaeopurpureus; Streptomyces purpeofuscus; Streptomyces showdoensis; Streptomyces tanashiensis; Streptomyces violaceorectus; Streptomyces zaomyceticus; Streptomyces aburaviensis; Streptomyces caeruleus; Streptomyces catenulae; Streptomyces chrysomallus* subsp. *fumigatus; Streptomyces xanthocidicus; Streptomyces achromogenes* subsp. *rubradiris; Streptomyces anandii, Streptomyces aurantiogriseus; Streptomyces bobili* subsp. *sporificans; Streptomyces cinerochromogenes; Streptomyces cirratus; Streptomyces collinus; Streptomyces eurythermus; Streptomyces galbus; Streptomyces galilaeus; Streptomyces griseoruber; Streptomyces griseosporeus; Streptomyces hygroscopicus* subsp. *ossamyceticus; Streptomyces kurssanovii; Streptomyces luteogriseus; Streptomyces massasporeus; Streptomyces mirabilis; Streptomyces multispiralis; Streptomyces naganishii; Streptomyces neyagawaensis; Streptomyces nojiriensis; Streptomyces olivochromogenes; Streptomyces phaeofaciens; Streptomyces pulveraceus; Streptomyces rameus; Streptomyces resistomycificus; Streptomyces rishiriensis; Streptomyces thermoviolaceus; Streptomyces violaceochromogenes; Streptomyces afghaniensis; Streptomyces arenae; Streptomyces attrocyaneus; Streptomyces chromofuscus; Streptomyces durhamensis; Streptomyces echinatus; Streptomyces filipinensis; Streptomyces fimbriatus; Streptomyces griseochromogenes; Streptomyces iakyrus; Streptomyces lucensis; Streptomyces malachitofuscus; Streptomyces malachitorectus; Streptomyces pilosus; Streptomyces albidofuscus; Streptomyces albogriseolus; Streptomyces ambofaciens; Streptomyces anthocyanicus; Streptomyces antimycoticus; Streptomyces argenteolus; Streptomyces atratus; Streptomyces aureofaciens; Streptomyces avellaneus; Streptomyces caesius; Streptomyces carnosus; Streptomyces chibaensis; Streptomyces coelescens; Streptomyces coelicolor* subsp. *achrous; Streptomyces coelicolor* subsp. *coelicofers; Streptomyces coelicolor* subsp. *coelicolatus; Streptomyces coelicolor* subsp. *coelicovarians; Streptomyces corchorusii; Streptomyces cyanogenus; Streptomyces diastaticus* subsp. *ardesiacus; Streptomyces diastatochromogenes* subsp. *bracus; Streptomyces endus; Streptomyces erumpens; Streptomyces griseoaurantiacus; Streptomyces griseofuscus; Streptomyces griseolosuffuscus; Streptomyces griseoluteus; Streptomyces griseus* subsp. *difficilis; Streptomyces humidus; Streptomyces hygroscopicus; Streptomyces hygroscopicus* subsp. *angustmyceticus; Streptomyces hygroscopicus* subsp. *decoyicus; Streptomyces hygroscopius* subsp. *glebosus; Streptomyces libani; Streptomyces libani* subsp. *rufus; Streptomyces lividans; Streptomyces lusitanus; Streptomyces lydicus; Streptomyces melanosporofaciens; Streptomyces misionensis; Streptomyces murinus; Streptomyces mutabilis; Streptomyces nigrescens; Streptomyces nodosus; Streptomyces nogalater; Streptomyces olivaceiscleroticus; Streptomyces olivaceoviridis; Streptomyces olivaceus; Streptomyces parvullus; Streptomyces platensis; Streptomyces plicatus; Streptomyces poonensis; Streptomyces psammoticus; Streptomyces purpurogeneiscleroticus; Streptomyces recifenis; Streptomyces rochei, Streptomyces rokugoensis; Streptomyces roseodiastaticus; Streptomyces rutgersensis* subsp. *castelarense; Streptomyces sayamaensis; Streptomyces sendaiensis; Streptomyces sioyaensis; Streptomyces tendae; Streptomyces thermovulgaris; Streptomyces tricolor; Streptomyces tubercidicus; Streptomyces tumemacerans; Streptomyces vastus; Streptomyces violaceolatus; Streptomyces violaceus-niger; Streptomyces violaceus-ruber; Streptomyces viridifaciens; Streptomyces atroolivaceus; Streptomyces cyanocolor; Streptomyces graminofaciens; Streptomyces griseoplanus; Streptomyces albaduncus; Streptomyces albospinus; Streptomyces albulus; Streptomyces althioticus; Streptomyces arabicus; Streptomyces atroolivaceus* subsp. *mutomycini; Streptomyces canus; Streptomyces chattanoogensis; Streptomyces chlorobiens; Streptomyces cuspidosporus; Streptomyces gancidicus; Streptomyces griseoflavus; Streptomyces griseoincarnatus; Streptomyces griseorubens; Streptomyces macrosporeus; Streptomyces malachiticus; Streptomyces matensis; Streptomyces noursei; Streptomyces olivoviridis; Streptomyces pseudogriseolus; Streptomyces rubiginosus; Streptomyces sparsogenes; Streptomyces viridiviolaceus; Streptomyces virido-diastaticus; Streptomyces calvus; Streptomyces cyanoalbus; Streptomyces finlayi, Streptomyces flaveolus; Streptomyces geysiriensis; Streptomyces herbiferis; Streptomyces pactum; Streptomyces akitaensis; Streptomyces akiyoshiensis; Streptomyces alanosinicus; Streptomyces albidus* subsp. *invertens; Streptomyces albochromogenes; Streptomyces ansochromogenes; Streptomyces ansochromogenes* subsp. *pallens; Streptomyces avidinii; Streptomyces carcinomycicus; Streptomyces castaneglobisporus; Streptomyces castaneus; Streptomyces cyanoflavus; Streptomyces djakartensis; Streptomyces erythrochromogenes* subsp. *narutoensis; Streptomyces glomerochromogenes; Streptomyces grisinus; Streptomyces haranomachiensis; Streptomyces hygrostaticus; Streptomyces insulatus; Streptomyces inversochromogenes; Streptomyces kitazuwaensis; Streptomyces mariensis; Streptomyces minutiscleroticus; Streptomyces mitakaensis; Streptomyces nigrogriseolus; Streptomyces ogaensis; Streptomyces piedadensis; Streptomyces regensis; Streptomyces robefuscus; Streptomyces robeus; Streptomyces robustrus; Streptomyces roseogriseolus; Streptomyces roseogriseus; Streptomyces sahachiroi; Streptomyces senoensis; Streptomyces tanashiensis* subsp. *cephalomyceticus; Streptomyces thermonitrificans; Streptomyces thermoviolaceus* subsp. *apingens; Streptomyces viridoniger; Streptomyces werraensis; Streptomyces alboflavus; Streptomyces bacillaris; Streptomyces cavourensis; Streptomyces cyaneofuscatus; Streptomyces fulvissimus; Streptomyces griseobrunneus; Streptomyces michiganensis; Streptomyces tsusimaensis; Streptomyces xanthochromogenus; Streptomyces albidoflavus; Streptomyces alboviridis; Streptomyces anulatus; Streptomyces badius; Streptomyces californicus; Streptomyces canescens; Streptomyces celluloflavus; Streptomyces cellulosae; Streptomyces champavatii, Streptomyces chrysomallus; Streptomyces citreofluorescens; Streptomyces coelicolor; Streptomyces felleus; Streptomyces fimicarius; Streptomyces floridae; Streptomyces fluorescens; Streptomyces globisporus; Streptomyces globisporus* subsp. *caucasi-* cus; *Streptomyces globisporus* subsp. *flavofuscus*; *Streptomyces globisporus* subsp. *vulgaris*; *Streptomyces gougerotii*; *Streptomyces griseinus*; *Streptomyces griseoloalbus*; *Streptomyces griseus*; *Streptomyces griseus* subsp. *alpha*; *Streptomyces griseus* subsp. *cretosus*; *Streptomyces griseus* subsp. *solvifaciens*; *Streptomyces intermedius*; *Streptomyces kanamyceticus*; *Streptomyces levoris*; *Streptomyces limosus*; *Streptomyces lipmanii*; *Streptomyces microflavus*; *Streptomyces odorifer*; *Streptomyces parvus*; *Streptomyces pluricolorescens*; *Streptomyces pneumonicus*; *Streptomyces praecox*; *Streptomyces puniceus*; *Streptomyces raffinosus*; *Streptomyces rutgersensis*; *Streptomyces sampsonii*; *Streptomyces setonii*; *Streptomyces sindenensis*; *Streptomyces sulphureus*; *Streptomyces willmorei*; *Streptomyces hawaiiensis*; *Streptomyces albohelvatus*; *Streptomyces aurigineus*; *Streptomyces canarius*; *Streptomyces chryseus*; *Streptomyces flavidovirens*; *Streptomyces helvaticus*; *Streptomyces longisporoflavus*; *Streptomyces niveus*; *Streptomyces paucidiastaticus*; *Streptomyces spheroides*; *Streptomyces pimprina*; *Streptomyces capoamus*; *Streptomyces cinnabarinus*; *Streptomyces crystallinus*; *Streptomyces flavotricini*; *Streptomyces gobitricini*; *Streptomyces lincolnensis*; *Streptomyces melanogenes*; *Streptomyces phaeochromogenes*; *Streptomyces phaeochromogenes* subsp. *chloromyceticus*; *Streptomyces pseudovenezuelae*; *Streptomyces roseoviridis*; *Streptomyces spectabilis*; *Streptomyces subrutilus*; *Streptomyces umbrinus*; *Streptomyces venezuelae*; *Streptomyces xanthophaeus*; *Streptomyces aureomonopodiales*; *Streptomyces exfoliatus*; *Streptomyces filamentosus*; *Streptomyces prunicolor*; *Streptomyces roseofulvus*; *Streptomyces roseolus*; *Streptomyces roseoporus*; *Streptomyces rubiginosohelvolus*; *Streptomyces termitum*; *Streptomyces cinnamonensis*; *Streptomyces colombiensis*; *Streptomyces goshikiensis*; *Streptomyces katrae*; *Streptomyces lavendofoliae*; *Streptomyces lavendulae*; *Streptomyces lavendulae* subsp. *avireus*; *Streptomyces lavendulae* subsp. *brasilicus*; *Streptomyces lavendulae* subsp. *grasserius*; *Streptomyces lavendulcolor*; *Streptomyces luridus*; *Streptomyces orchidaceus*; *Streptomyces racemochromogenes*; *Streptomyces syringae*; *Streptomyces toxytricini*; *Streptomyces tuirus*; *Streptomyces vinaceus*; *Streptomyces virginiae*; *Streptomyces lateritus*; *Streptomyces flavovariabilis*; *Streptomyces janthinus*; *Streptomyces purpurascens*; *Streptomyces roseospinus*; *Streptomyces roseoviolaceus*; *Streptomyces violaceus*; *Streptomyces violaceus* subsp. *confinus*; *Streptomyces violaceus* subsp. *vicinus*; *Streptomyces violarus*; *Streptomyces violatus*; *Streptomyces yokosukanensis*; *Streptomyces albosporeus*; *Streptomyces aurantiacus*; *Streptomyces aureoverticillatus*; *Streptomyces aurini*; *Streptomyces cremeus*; *Streptomyces daghestanicus*; *Streptomyces fradiae*; *Streptomyces fragilis*; *Streptomyces fumanus*; *Streptomyces glomeroaurantiacus*; *Streptomyces griseoviridis*; *Streptomyces niveoruber*; *Streptomyces peucetius*; *Streptomyces phaeoviridis*; *Streptomyces roseisclerotius*; *Streptomyces roseoflavus*; *Streptomyces roseolilacinus*; *Streptomyces rubo-cyaneus*; *Streptomyces tauricus*; *Streptomyces vinaceus-drappus*; *Streptomyces virocidus*; *Streptomyces erythraeus*; *Streptomyces luteofluorescens*; *Streptomyces erythrogriseus*; *Streptomyces garyphalus*; *Streptomyces lavendularectus*; *Streptomyces nagasakiensis*; *Streptomyces rubrolavendulae*; *Streptomyces cinnamonensis*; *Streptomyces ashchabadicus*; *Streptomyces polychromogenes*; *Streptomyces amakusaensis*; *Streptomyces caelestis*; *Streptomyces azureus*; *Streptomyces bellus*; *Streptomyces chartreusis*; *Streptomyces coeliatus*; *Streptomyces coerulatus*; *Streptomyces coerulatus* subsp. *amylolyticus*; *Streptomyces coeruleofuscus*; *Streptomyces coeruleorubidus*; *Streptomyces coerulescens*; *Streptomyces curacoi*; *Streptomyces cyaneus*; *Streptomyces cyanoglomerus*; *Streptomyces indigocolor*; *Streptomyces lanatus*; *Streptomyces lazureus*; *Streptomyces valynus*; *Streptomyces viridochromogenes*; *Streptomyces glaucescens*; *Streptomyces blensis*; *Streptomyces coerulatus* subsp. *anaseul*; *Streptomyces coeruleoroseus*; *Streptomyces ipomoeae*; *Streptomyces spinosus*; *Streptomyces griseomycini*; *Streptomyces griseostramineus*; *Streptomyces prasinosporus*; *Streptomyces ghanaensis*; *Streptomyces hirsutus*; *Streptomyces prasinus*; *Streptomyces viridosporus*; *Streptomyces acrimycini*; *Streptomyces bambergiensis*; *Streptomyces prasinopilosus*; *Streptomyces horton*; *Streptomyces rectiviolaceus*; *Streptomyces lilacinofulvus*; *Streptomyces mauvecolor*; *Streptomyces violans*; *Streptomyces violascens*; *Streptoverticillium baldaccii*; *Streptoverticillium fervens*; *Streptoverticillium rubrochlorinum*; *Streptoverticillium biverticillatum*; *Streptoverticillium aureoversales*; *Streptoverticillium pentaticum*; *Streptoverticillium roseoverticillatum*; *Streptoverticillium rubroverticiflatum*; *Streptoverticillium hiroshimense*; *Streptoverticillium salmonis*; *Streptoverticillium luteoverticillatum*; *Streptoverticillium olivoreticuli*; *Streptoverticillium waksmanii*; *Streptoverticillium griseocarneum*; *Streptoverticillium cinnamoneum*; *Streptoverticillium hachijoense*; *Streptoverticillium ardum*; *Streptoverticillium abikoense*; *Streptoverticillium albireticuli*; *Streptoverticillium eurocidicum*; *Streptoverticillium kishiwadense*; *Streptoverticillium mashuense*; *Streptoverticillium olivoverticillatum*; *Streptoverticillium orinoci*; *Streptoverticillium parvisporogenes*; *Streptoverticillium kentuckense*; *Streptoverticillium album*; *Streptoverticillium distallicum*; *Streptoverticillium ehimense*; *Streptoverticillium flavopersicum*; *Streptoverticillium griseoverticillatum*; *Streptoverticillium netropsis*; *Streptoverticillium rectiverticillatum*; *Streptoverticillium septatum*; *Streptoverticillium mobaraense*; *Streptoverticillium blastmyceticum*; *Streptoverticillium lavenduligriseum*; *Streptoverticillium lilacinum*; *Streptoverticillium kashmirense*; *Streptoverticillium thioluteum*; *Sporichthya polymorpha*; *Microellobosporia cinerea*; *Microellobosporia violacea*; *Microellobosporia flavea*; *Microellobosporia grisea*; *Micromonospora chalcea*; *Micromonospora halophytica*; *Micromonospora carbonacea*; *Micromonospora narashinoensis*, *Micromonospora melanosporea*; *Micromonospora echinospora*; *Micromonospora purpurea*; *Micromonospora purpureochromogenes*; *Micromonospora bicolor*; *Micromonospora coerulea*; *Micromonospora globosa*; *Micromonospora elongata*; *Micromonospora parva*; *Micromonospora gallica*; *Micromonospora acetoformici*; *Micromonospora propionici*; *Thermoactinomyces vulgaris*; *Thermoactinomyces sacchari*; *Actinobifida dichotomica*; *Actinobifida alba*; *Actinobifida chromogena*; *Thermomonspora curvata*; *Thermomonospora viridis*; *Microbispora rosea*; *Microbispora aerata*; *Microbispora amethystogenes*; *Microbispora bispora*; *Microbispora chromogenes*; *Microbispora diastatica*; *Microbispora parva*; *Microbispora thermodiastatica*; *Microbispora thermorosea*; *Micropolyspora brevicatena*; *Micropolyspora angiospora*; *Micropolyspora caesia*; *Micropolyspora faeni*; *Micropolyspora rectivirgula*; *Micropolyspora rubrobrunea*; *Micropolyspora thermovirida*; and *Micropolyspora viridinigra*.

The microparticle calcium phosphate having a size phagocytizable by cells may carry an antigen together with or apart from the immunostimulating substance. Types of the antigen used for such purpose are not particularly limited so long as they can be carried by the microparticle calcium phosphate are used. For example, bovine serum albumin, which is water-soluble and highly soluble, can be carried as the antigen (Japanese Patent Unexamined Publication (KOKAI) No.

2005-126335). Further, a hydrophobic substance can also be carried as the antigen in the same manner as that used for the aforementioned soluble ingredients derived from microorganisms. The antigen preferably consists of one kind or two or more kinds of antigens selected from the group consisting of fungi, Actinomycetes, bacteria, viruses, phages, rickettsias, protozoans, ingredients of these microorganisms, ingredients of protozoans, tumor tissues, tumor cells, tumor cell ingredients, tumor antigen proteins and tumor antigen peptides, but not limited to these examples.

The method for preparing microparticle precipitates by coacervation of a soluble protein and a mucopolysaccharide is described in detail, for example, in U.S. Pat. No. 5,759,582, and the those skilled in the art can easily prepare the aforementioned precipitates. For example, the method of using (i) albumin as the soluble protein, (ii) heparin as the mucopolysaccharide, and (iii) PPD as the immunostimulating substance is described in detail in Japanese Patent No. 3,492,671, and the method is most preferably used. However, the method is not limited to this example. The combination of the soluble protein and the mucopolysaccharide is not limited to the aforementioned combination. As the immunostimulating substance, for example, soluble proteins contained in tuberculin may be used, and all or a part of soluble proteins prepared from tuberculin by a method well known to those skilled in the art can also be used. By mixing the aforementioned three ingredients (i), (ii) and (iii) mentioned above by stirring, precipitates are formed by coacervation of the ingredient (i) and the ingredient (ii), and during the formation of the precipitates, the ingredient (iii) is incorporated into the precipitates and coprecipitated to give precipitates. The precipitates formed by coacervation of the soluble protein and the mucopolysaccharide are preferably prepared in the shape of microparticle having such a size that the microparticle can pass through an injection needle from a viewpoint of convenience of administration. The particle size of the microparticle is generally preferred to be 1 μm or smaller. As the method of preparing the precipitates in the shape of a microparticle, a method well known to those skilled in the art may be used, and the method is not limited to any specific method.

The ratio of the soluble proteins contained in the immunostimulating substance and the soluble protein of (i) is not particularly limited, and it may be any ratio so long as coacervation of the soluble protein of (i) and the mucopolysaccharide of (ii) is caused. For example, when a 2.5% human serum albumin solution at pH 2.5 is used as the soluble protein, a commercially available about 5 mg/ml heparin solution is used as the mucopolysaccharide, PPD is dissolved in the solution in an amount of 2.5 μg per 600 μl of the mucopolysaccharide, and then the mixture is added dropwise with the aforementioned human serum albumin solution with stirring to form microparticles by coacervation. The ratio is preferably chosen as such a volume ratio that most of the mixed proteins should be incorporated into the microparticles as determined by centrifuging the suspension obtained above and quantifying proteins in the supernatant. However, it can be understood that the ratio of the ingredient (i) or (iii), conditions of the coacervation and the like can be suitably chosen by those skilled in the art. Although the particle size of the microparticles contained in the obtained precipitates is usually about 1 μm, the size is not limited to any specific size.

Although the resulting microparticle precipitates without any treatment can be used as a carrier carrying the immunostimulating substance as one ingredient of the adjuvant of the present invention, the precipitates may be washed with distilled water, if needed. In order to stabilize the precipitates, an inter-protein molecule crosslinking agent may be reacted on the precipitates to form crosslinkages and thereby form insoluble microparticles. Type of the inter-protein molecule crosslinking agent is not particularly limited, and crosslinking agents well known to those skilled in the art can be used in a well-known manner. For example, 1-ethyl-3-(3-dimethylaminopropyl)-carbodiimide is prepared as a 20 mg/ml aqueous solution, and added at a final concentration of 0.8 to 1.5 mg/ml with stirring by a vortex mixer, and then the mixture is left standing at room temperature for 15 minutes. Thus, sufficiently stable crosslinkages are formed between the protein molecules in the precipitates. However, the means for the formation of crosslinkages is not limited to the aforementioned specific conditions or the specific inter-protein molecule crosslinking agent. The microparticle precipitates obtained as described above, preferably such microparticle precipitates further subjected to a crosslinking treatment, are not dissolved even if they are washed with water, and can be preferably used as the ingredient of the adjuvant of the present invention.

According to a preferred embodiment, an antigenic soluble protein and tuberculin soluble proteins having an immunoadjuvant activity can be mixed beforehand, and this mixture can be used instead of the ingredient (iii) mentioned above to obtain precipitates in the same manner as that mentioned above. These precipitates correspond to a carrier carrying the immunostimulating substance and the antigen, and can also be used as one ingredient of the adjuvant of the present invention.

The precipitates obtained by coacervation of a soluble protein and a mucopolysaccharide may carry an antigen together with or apart from the immunostimulating substance. As the antigen, for example, inducers including cytokines, chemokines, cells growth factors, and hormones can also be used. As the antigen, one kind or two or more kinds of substances selected from the group consisting of tuberculin, PPD, soluble ingredients originating in microorganisms, trehalose 6,6'-dimycolate, LPS, lipid A, oligonucleotides, β-glucans, keyhole limpet hemocyanin, muramyl dipeptide, bestatin, levamisole, cytokines, chemokines, cell growth factors and hormones can also be used. Furthermore, one kind or two or more kinds of extracts selected from the group consisting of alcohol extracts, acetone extracts, pyridine extracts and hot water extracts of microorganisms can also be used as the antigen. As the microorganism, bacteria are preferred, and it is more preferred that the extract is bound to soluble proteins. As the microorganism, those exemplified above are preferably used. However, the antigen to be carried by the precipitates obtained by the coacervation of a soluble protein and a mucopolysaccharide is not limited to the aforementioned specific examples.

The precipitates obtained by coacervation of a soluble protein and a mucopolysaccharide and other insoluble protein molecules or antigen can also be crosslinked with an inter-protein molecule crosslinking agent to prepare the carrier carrying the immunostimulating substance in the form of insoluble microparticle. Type of the inter-protein molecule crosslinking agent is not particularly limited, and crosslinking agents well known to those skilled in the art can be used in a well-known manner. For example, 1-ethyl-3-(3-dimethylaminopropyl)carbodiimide and the like can be used.

Immunoadjuvant activity of the immunoadjuvant of the present invention can be easily measured by those skilled in the art by using the method specifically explained in the specification of the present invention and the method explained below. The THP-1 cell line is an established cell line of human-derived macrophage, and it is known that when phorbol 12-myristate 13-acetate (henceforth also abbreviated as "PMA") acted on cells of the strain during culture to induce differentiation, the cells exhibit phagocytic ability (Kurosaka, K., et al., J. Immunol., 161, pp. 6245-6249, 1998), and become antigen-presenting cells (Hu, P. Q., et al., J. Immunol., 172, pp. 1595-1601, 2004). When these cells are pretreated with IFNg, the antigen presentation ability to T cells is enhanced (Brett, S. J., et al., J. Immunol., 150, pp. 2869-84, 1993). Therefore, by differentiating the THP-1 cells and quantifying produced GM-CSF, it is possible to measure degree of activation of human antigen-presenting cells without using peripheral blood-derived adherent cells including human antigen-presenting cells. Since the THP-1 cell is an established cell line, a qualitatively stable test material can be secured regardless of the variation of human individuals.

The immunoadjuvant of the present invention can be mixed with an antigen and internally administered to a mammal including human to induce a systemic immune response to the antigen, and can be used in the same manner as that for usually used general immunoadjuvants. As the antigen, an organism or substance which does not originally exist in an individual to be administered can be used, and more specifically, for example, one kind or two or more kinds of substances selected from the group consisting of fungi, Actinomycetes, bacteria, viruses, phages, rickettsias, protozoans, ingredients of these microorganisms, tumor tissues, tumor cells, tumor cell ingredients, tumor antigen proteins and tumor antigen peptides can be used as the antigen. However, the antigen is not limited to these examples, and any substances that can act as an antigen may be used. Further, by internally administering an antigen as an independent formulation to a mammal including human, and internally administering the immunoadjuvant of the present invention separately, a systemic immune response to the antigen can also be induced. Furthermore, as explained above, the antigen may be carried on any one or two or more of the two or more kinds of immunostimulating substance carriers as the ingredient of the immunoadjuvant of the present invention, and even in such a case, the antigen may be separately administered.

When the antigen consists of a fungus, Actinomycete, bacterium, virus, phage, rickettsia, protozoan and/or ingredient of these microorganisms, a vaccine therapy for prophylactic and/or therapeutic treatment of an infectious disease can be performed by administering the immunoadjuvant of the present invention and the antigen. Further, when the antigen is a tumor tissue, tumor cell, tumor cell ingredient and/or tumor antigen peptide, a vaccine therapy for prophylactic and/or therapeutic treatment of a tumor can be performed by administering the immunoadjuvant of the present invention together with the aforementioned antigen. For example, by administering a mixture of tumor cells isolated from a patient and inactivated together with the immunoadjuvant of the present invention to the patient, an antitumor immune response to the tumor cells can be induced in the living body of the patient. However, the method for use of the mixed immunoadjuvant formulation of the present invention is not limited to the aforementioned embodiments, and any usual method using an immunoadjuvant may be used. Although dose and administration method of the immunoadjuvant of the present invention are not particularly limited, it can generally be administered by parenteral administration such as injections (subcutaneous injection and the like) so that an immune response can be sufficiently induced.

Further, by denaturing a tumor tissue in the body of patient with a physical means and then administering the immunoadjuvant of the present invention into the tissue, an antitumor immune response can be induced to tumor surviving in the body of the patient. Although the means for the physical denaturation of the tumor tissue is not particularly limited, for example, means including microwave irradiation, radiofrequency ablation, cryoablation, electrotome heating, hot water injection, alcohol injection, embolization, radiation exposure, laser beam irradiation, sonic disruption, and the like can be employed. However, the physical denaturation means is not limited to these examples, and any means that can induce cell death of tumor cells in a tumor tissue can be used. Two or more kinds of physical means may be suitably combined.

For example, if a tumor tissue is thermally solidified by microwave irradiation, and the immunoadjuvant of the present invention is administered into the solidified tissue, an antitumor immune response can be induced to tumor cells surviving in the tumor tissue and surrounding portions. It is also preferable to simultaneously administer a tuberculin solution at the time of administration of the immunoadjuvant of the present invention. However, the administration method of the immunoadjuvant of the present invention is not limited to the aforementioned embodiments, and any method may be employed so long as such environment is given that the immunoadjuvant of the present invention can be incorporated into the antigen-presenting cells gathering in the denatured tumor tissue together with the tumor antigen, or the immunoadjuvant of the present invention can directly stimulate the antigen-presenting cells.

Further, by mixing the immunoadjuvant of the present invention and immunocompetent cells outside the body beforehand, and internally administering the mixture to a patient, an immune response can also be stimulated in the body. As the immunocompetent cells, dendritic cells, B lymphocytes, T lymphocytes, natural killer cells, and/or hematopoietic stem cells, and the like can be preferably used. However, the immunocompetent cells are not limited to these examples.

From another aspect, a vaccine containing the immunoadjuvant of the present invention and an antigen as active ingredients is provided by the present invention. For the administration of this vaccine, a method well known to those skilled in the art may be used, and immunocompetent cells may be simultaneously mixed. By using, for example, a substance derived from a source of infection which has caused an infectious disease such as viruses and viral ingredients as the antigen, prophylaxis of the infection in non-infected patients, as well as therapeutic treatment for patients already suffering the infectious disease, can be performed. By administering a vaccine containing one kind or two or more kinds of biological samples selected from the group consisting of tumor tissues, tumor cells, tumor cell ingredients, tumor antigen proteins, and tumor antigen peptides isolated from a patient together with the aforementioned immunoadjuvant to the patient from whom the tumor is derived, the tumor can also be treated.

Furthermore, when the antigen is a foreign protein, for example, by administering the antigen to an animal other than human together with the aforementioned immunoadjuvant, the host animal can be made to efficiently produce antibodies directed to the antigen. By this method, an antibody-producing animal can be easily prepared, and antibody-producing cells and antibody genes derived from the antibody-producing animal can also be easily obtained. The antigen may be any substance so long as the substance has antigenicity to the host, but not limited to those mentioned above.

EXAMPLES

Hereafter, the present invention will be explained more specifically by way of examples. However, the scope of the present invention is not limited to the following examples.

Example 1

Antigen-Presenting Cell Stimulating Effect of Immunoadjuvant in which One Kind of Immunostimulating Substance is Carried on Two Kinds of Immunostimulating Substance Carriers Cells of the THP-1 cell line were differentiated with PMA and thereby made into antigen-presenting cells, and PPD was carried on two kinds of immunostimulating substance carriers. The carriers were added to the antigen-presenting cells under the culture condition, and the production amount of GM-CSF was measured.

A. Materials and Methods

1. Preparation of Calcium Phosphate (Henceforth Abbreviated as "CaP") Microparticle Nucleus Suspension Calcium carbonate $CaCO_3$ (purity: 99.99%, Calceed) was weighed in an amount corresponding to 2 moles, put into a high purity alumina sagger, and calcined at 1000° C. for 3 hours in a box furnace to perform decarboxylation and thereby obtain calcium oxide CaO of high purity, which was put into a beaker. In order to suppress a reaction of CaO and moisture in air and further reaction with carbon dioxide as much as possible, the upper part of the beaker was closed with a wrap, and the beaker was placed in a polyethylene container having an internal volume of 10 L as a reaction vessel. The inside of the container was impregnated with nitrogen gas, then the wrap of the beaker was removed, and ultrapure water was added dropwise into the beaker. During this operation, in order to protect the beaker from heat generation, ultrapure water was also filled in the polyethylene container. When the heat of the reaction settled down, all the reactants in the beaker were flushed with ultrapure water and transferred into the polyethylene container. The total volume of the ultrapure water used above was adjusted so that the concentration calculated from the amount of CaO became 0.5 mol/L. At this stage, a calcium hydroxide $Ca(OH)_2$ suspension was obtained. This suspension stirred at about 500 rpm with a stirrer (MAZELA Z-1000, EYELA) was added dropwise with 2 L of orthophosphoric acid $H_2PO_4$ (concentration: 85%, Kokusan Chemical) prepared at 0.6 mol/L at a rate not exceeding 25 mL/min. After completion of the addition, the mixture was stirred for 24 hours as it was to obtain a CaP nucleus suspension.

2. Preparation of CaP Microparticle Suspension and CaP-PPD Microparticle Suspension 2.1 Preparation of Calcium Phosphate Supersaturated Solution and CaP Microparticle Suspension Ringer's solution (Fuso Pharmaceutical Industries), Klinisalz B solution (Kobayashi Pharmaceutical Industries) and a sodium hydrogencarbonate replenisher for exclusive use for Bifil (Shimizu Pharmaceutical) were mixed in volumes of 8.28 mL, 1.24 mL and 0.48 mL, respectively, to obtain a volume of 10 mL. To 9 mL of this calcium phosphate supersaturated solution, 1 mL of ethanol was added, one drop of CaP microparticle nucleus suspension was added per 10 mL of the mixture, and the mixture was left overnight. The suspension was centrifuged to obtain precipitates, and the precipitates were sufficiently washed with physiological saline for injection, and suspended in 1 mL of physiological saline for injection. This was used as a CaP microparticle suspension.

2.2 Preparation of CaP-PPD Microparticle Suspension

The Ringer's solution, Klinisalz B solution and sodium hydrogencarbonate replenisher for exclusive use for Bifil were mixed in volumes of 8.28 mL, 1.24 mL and 0.48 mL, respectively, to obtain a volume of 10 mL. In 9 mL of this calcium phosphate supersaturated solution, 0.5 μg or 10 μg of standard tuberculin (tuberculin purified protein derivative for general diagnosis (PPD), Japan BCG Laboratory) was dissolved. To 9 mL of this solution, 1 mL of ethanol was added, one drop of CaP microparticle nucleus suspension was added per 10 mL of the mixture, and the mixture was left overnight. The suspension was centrifuged to obtain precipitates, and the precipitates were sufficiently washed with physiological saline for injection, and suspended in 1 mL of physiological saline for injection. Each CaP-PPD microparticle suspension obtained here is indicated as CaP-PPD (0.5 μg/mL) or CaP-PPD (10 μg/mL) according to the amount of PPD used for the preparation. Further, when the final concentrations of these added to culture medium (RPMI 1640 medium containing 10% fetal bovine serum) corresponded to ⅕ of these, each is indicated as CaP-PPD (0.1 μg/mL) or CaP-PPD (2.0 μg/mL).

2.3 Preparation of PPD Solution

Standard tuberculin (tuberculin purified protein derivative for general diagnosis (PPD), Japan BCG Laboratory) in an amount of 0.25 μg was dissolved in 0.5 mL of the culture medium to obtain a PPD solution.

2.4 Preparation of PPD-Carrying Coacervation-Precipitated Microparticle Suspension (Henceforth Abbreviated as "TuMP")

1) A 25% human serum albumin solution (HSA, Baxter Albumac, Baxter) was diluted to 2.5% with sterilized water, and adjusted to pH 2.5 with 4 N HCl.

2) The 2.5% human serum albumin solution and a heparin solution (Novo-Heparin Injection 1000, 1000 unit/mL, about 7.69 mg/mL or less, Aventis Pharma) were mixed beforehand at various ratios, and an optimum mixing ratio of the heparin solution was determined. First, microparticles were prepared at an arbitrary mixing ratio, the suspension was centrifuged at 2,500 rpm (1300 g) for 15 minutes, and protein content of the supernatant was quantified with Protein Assay Kit 1 (Nippon Bio-Rad Laboratories, Tokyo). The optimum mixing ratio was defined to be such a ratio that 99.9% or more of the mixed proteins should be incorporated into the microparticles.

3) PPD was suspended in the heparin solution for injection, and the suspension was added dropwise with the 2.5% human serum albumin solution at a predetermined ratio with stirring by a vortex mixer.

4) The mixture was centrifuged at 4,300 rpm (1300 g) for 15 minutes, and the precipitates were washed twice with distilled water, and resuspended in distilled water.

5) A 1-ethyl-3-(3-dimethylaminopropyl)carbodiimide solution (EDC, SIGMA, 20 mg/mL solution in water) was added to the suspension at a final concentration of 0.8 to 1.5 mg/mL with stirring by a vortex mixer, and then the mixture was left standing at room temperature for 15 minutes.

6) An equal volume of 0.1 M glycine aqueous solution was added to the mixture, and the mixture was left standing at room temperature for 15 minutes.

7) The mixture was centrifuged at 4,300 rpm (1300 g) for 15 minutes, and the precipitates were washed 3 times with distilled water, and resuspended in physiological saline at a concentration of 0.5 µg/mL in terms of PPD.

This suspension was used as a TuMP suspension.

2.5 Preparation of LPS Solution

Lipopolysaccharide (henceforth referred to as "LPS", Sigma-Aldrich Japan, Tokyo) was dissolved in Dulbecco's phosphate buffered saline not containing calcium and magnesium (henceforth referred to as "PBS(−)", SIGMA) at 1 mg/mL.

2.6 Differentiation-Inducing Culture of THP-1 Cell Line and GM-CSF Production Test Cells of human macrophage-like cell line THP-1 were collected by centrifugation, and washed twice with PBS(−), and the cell count was adjusted to 4,000,000 cells/mL in a culture medium (RPMI 1640 medium containing 10% fetal bovine serum). The cell suspension was added with a PMA solution (prepared by dissolving PMA produced by SIGMA in DMSO at 1.62 mM) at a final concentration of 1.6 µM, and inoculated in a volume of 0.5 mL to each well of a 24-well plate, and culture was performed for four days. After the culture, the cells were washed twice with PBS, the medium was exchanged with fresh culture medium, and culture was further performed overnight. Then, the medium was exchanged with 0.5 mL of each of various culture media for stimulation. In the preparation of these 0.5 mL media, the CaP microparticle suspension and the CaP-PPD microparticle suspension were added in a ⅕ volume. Further, PPD was added as a 0.5 µg/mL solution in the culture medium in a ⅕ volume. The TuMP suspension (2.5 µg/mL) was added in a 1/25 volume. The LPS solution was diluted with the culture medium and added so that the final concentrations should be the concentrations mentioned in Table 1. The final concentrations of these substances are shown in Table 1.

2.6 Samples for GM-CSF Measurement

After exchanging the medium with 0.5 mL each of the various culture media for stimulation, the cells were cultured for 24 hours, and the culture supernatants were collected and used as samples for GM-CSF measurement.

3. Quantification of GM-CSF

A kit for quantification of human GM-CSF (Human GM-CSF ELISA System Biotrak, Amersham LIFE SCIENCE) was used according to the instructions of the kit. The quantification of GM-CSF was performed in duplicate. Absorbance was measured at 450 nm within 30 minutes by using a microplate reader (Biotrak II, Amersham Biosciences), and values of GM-CSF were calculated by using a calibration curve.

B. Results

The results are shown in Table 1. The abbreviations used in the table have the following meanings: CaP: calcium phosphate microparticles, PPD: tuberculin purified protein derivative (final concentrations are mentioned in the parentheses), TuMP: PPD-carrying coacervation precipitate microparticles (final concentrations of carried PPD are mentioned in the parentheses), CaP-PPD: PPD-carrying calcium phosphate microparticles (final concentrations of carried PPD are mentioned in the parentheses), and LPS: lipopolysaccharide (final concentrations are mentioned in the parentheses). The amounts of GM-CSF produced by this test system gave quantitatively dose-dependent response to the added LPS concentration. Therefore, the test system had a superior quantification performance. THP-1 cells which became antigen-presenting cells by differentiation produced only an extremely small amount of GM-CSF, even when they were stimulated with PPD, TuMP or both. Whilst CaP-PPD allowed GM-CSF production 3 times at a concentration of 0.1 µg/mL and 13 times at a concentration of 2.0 µg/mL higher than that of the no stimulation case. Further, when PPD and TuMP were further added to CaP-PPD, GM-CSF was produced in an amount larger than the amount obtained by simply adding the concentrations of GM-CSF produced by independently adding CaP-PPD, PPD and TuMP. Such effects exceeding additive effect were observed for all the concentrations of CaP-PPD, 0.1, 0.4 and 2.0 µg/mL, and stronger expression was observed at a higher CaP-PPD concentration. Thus, a synergistic effect was confirmed.

TABLE 1

| No. | Immunostimulating substance | Produced GM-CSF (ng/ml) |
| --- | --- | --- |
| 1 | No stimulation | 1.7 |
| 2 | PPD (0.1 µg/mL) | 2.9 |
| 3 | TuMP (0.1 µg/mL) | 2.5 |
| 4 | PPD (0.1 µg/mL) + TuMP (0.1 µg/mL) | 2.8 |
| 5 | CaP-PPD (0.1 µg/mL) | 5.1 |
| 6 | CaP-PPD (0.4 µg/mL) | 6.4 |
| 7 | CaP-PPD (2.0 µg/mL) | 22.2 |
| 8 | CaP-PPD (0.1 µg/mL) + PPD (0.1 µg/mL) + TuMP (0.1 µg/mL) | 12.4 |
| 9 | CaP-PPD (0.4 µg/mL) + PPD (0.1 µg/mL) + TuMP (0.1 µg/mL) | 14.3 |
| 10 | CaP-PPD (2.0 µg/mL) + PPD (0.1 µg/mL) + TuMP (0.1 µg/mL) | 67.7 |
| 11 | LPS (10 ng/mL) | 34.1 |
| 12 | LPS (100 ng/mL) | 65.2 |
| 13 | LPS (1000 ng/mL) | 131.3 |

Example 2

Antigen-Presenting Cell Stimulating Effect of Immunoadjuvant in which Two Kind of Immunostimulating Substances are Carried Independently on Separate Immunostimulating Substance Carriers A. Materials and Methods Preparation of Reagents, Culture for Inducing Differentiation of Cells of the THP-1 cell line, GM-CSF production test, preparation of samples for GM-CSF measurement, and quantification of GM-CSF were performed according to the procedures of Example 1. Preparation of the other reagents was performed as follows.

1. Preparation of BCG Bacterium Extract-Carrying Calcium Phosphate Microparticle (Henceforth Abbreviated as "CaP-Bx") Suspension 1) Dry BCG vaccine (Japan BCG Laboratory) in 1 ampoule (12 mg) was autoclaved for 5 minutes at 110° C., and added with 1 mL of ethanol, and the mixture was stirred for 6 hours or longer. Then, the suspension was collected and added to the dry BCG formulation of another ampoule, the mixture was sufficiently stirred, and centrifuged at 12,000 rpm for 5 minutes in an Eppendorf-type high speed microcentrifuge, and the supernatant was collected as a BCG cell-derived ethanol soluble ingredient solution (henceforth referred to as "BCG extract").

2) The Ringer's solution, Klinisalz B solution and sodium hydrogencarbonate replenisher for exclusive use for Bifil were mixed in volumes of 8.28 mL, 1.24 mL and 0.48 mL, respectively, to obtain a volume of 10 mL. To 9 mL of this calcium phosphate supersaturated solution, 1 mL of the BCG extract was added, and one drop of CaP microparticle nucleus suspension was added per 10 mL of the mixture, and the mixture was left overnight. The suspension was centrifuged to obtain precipitates, and the precipitates were sufficiently washed with physiological saline for injection, and suspended in 1 mL of physiological saline for injection. This suspension was used as CaP-Bx suspension. In the GM-CSF production test, the suspension was added in a 1/5 volume to the culture medium for stimulation.

B. Results

The results are shown in FIG. 1. The vertical lines on the bars of Nos. 10, 11 and 12 in the bar graph represent standard deviations. The abbreviations used in the graph have the following meanings: CaP: calcium phosphate microparticles, PPD: tuberculin purified protein derivative (final concentration was 0.1 µg/mL), TuMP: PPD-carrying coacervation precipitate microparticles (final concentration of carried PPD was 0.1 µg/mL), CaP-Bx: BCG bacterium extract-carrying calcium phosphate microparticles (for the preparation method and final concentration of BCG bacterium extract, refer to A 1.1 mentioned above), and LPS: lipopolysaccharide (final concentrations are mentioned in the parentheses). The immunostimulating substances in the samples mentioned in the graph are shown in Table 2 below.

TABLE 2

| No. | Immunostimulating substance |
|---|---|
| 1 | No stimulation |
| 2 | CaP |
| 3 | TuMP |
| 4 | PPD |
| 5 | PPD + TuMP |
| 6 | CaP + TuMP |
| 7 | CaP + PPD |
| 8 | CaP + PPD + TuMP |
| 9 | CaP-Bx |
| 10 | CaP-Bx + TuMP |
| 11 | CaP-Bx + PPD |
| 12 | CaP-Bx + PPD + TuMP |
| 13 | LPS (10 ng/mL) |
| 14 | LPS (100 ng/mL) |
| 15 | LPS (1000 ng/mL) |

Antigen-presenting cell stimulating action was not observed for the CaP microparticles as the carrier. TuMP and PPD gave only an extremely weak stimulation action as in Example 1, and even when CaP, TuMP and PPD were mixed, the stimulation action of the mixture was weak, and the maximum GM-CSF production amount was 12.4 ng/mL (No. 5). CaP-Bx gave the amount of 128.7 ng/mL (No. 9), and when TuMP was added to this sample, a definite synergistic effect was observed (No. 10 and No. 12), although the amount did not substantially change even when PPD was added to the same sample.

Example 3

Antigen-Presenting Cell Stimulating Effect of Immunoadjuvant in which Two Kind of Immunostimulating Substances are Carried on One Kind of Immunostimulating Substance Carrier, and One Kind of Immunostimulating Substance is Carried on Another Immunostimulating Substance Carrier A. Materials and Methods Preparation of Reagents, Culture for Inducing Differentiation of Cells of the THP-1 cell line, GM-CSF production test, preparation of samples for GM-CSF measurement, and quantification of GM-CSF were performed according to the procedures of Example 1. Preparation of the other reagents was performed as follows.

1. Preparation of PPD-BCG Bacterium Extract-Carrying Calcium Phosphate Microparticle (Henceforth Abbreviated as "CaP-PPD-Bx") Suspension 1) The Ringer's solution, Klinisalz B solution and sodium hydrogencarbonate replenisher for exclusive use for Bifil were mixed in volumes of 8.28 mL, 1.24 mL and 0.48 mL, respectively, to obtain a volume of 10 mL. In 9 mL of this calcium phosphate supersaturated solution, 5 µg of PPD was dissolved. To 9 mL of this solution, 1 mL of the BCG extract was added, one drop of CaP microparticle nucleus suspension was added per 10 mL of the mixture, and the mixture was left overnight. The suspension was centrifuged to obtain precipitates, and the precipitates were sufficiently washed with physiological saline for injection, and suspended in 1 mL of physiological saline for injection. This suspension was used as CaP-PPD-Bx suspension. In the GM-CSF production test, the suspension was added in a 1/5 volume to the culture medium for stimulation.

B. Results

The result are shown in Table 3. The abbreviations used in the table have the following meanings: CaP: calcium phosphate microparticles, PPD: tuberculin purified protein derivative (final concentration was 0.1 µg/mL), TuMP: PPD-carrying coacervation precipitate microparticles (final concentration of carried PPD was 0.1 µg/mL), CaP-PPD: PPD-carrying calcium phosphate microparticles (final concentration of carried PPD was 1.0 µg/mL); CaP-PPD-Bx: PPD and BCG bacterium extract-simultaneously carrying calcium phosphate microparticles (for the preparation method and final concentration, refer to A 1.1 mentioned above, final concentration of carried PPD was 1.0 µg/mL), and LPS: lipopolysaccharide (final concentrations are mentioned in the parentheses). Among the samples mentioned in Table 3, No. 8 was for confirming reproducibility of the results of Example 1, and when PPD and TuMP were added to CaP-PPD, GM-CSF was produced in an amount larger than the amount obtained by simply adding the concentrations of GM-CSF produced by adding CaP-PPD, PPD and TuMP independently. Therefore, it was confirmed that good reproducibility was obtained. For No. 7, which corresponds to the above sample not containing the PPD solution, a synergistic effect was similarly observed. In addition, also for the sample in which TuMP was added to CaP-PPD-Bx, an extremely strong synergistic effect was observed.

TABLE 3

| No. | Immunostimulating substance | Produced GM-CSF (ng/mL) |
| --- | --- | --- |
| 1 | No stimulation | 1.0 |
| 2 | PPD | 0.3 |
| 3 | TuMP | 0.6 |
| 4 | PPD + TuMP | 1.2 |
| 5 | CaP-PPD | 11.4 |
| 6 | CaP-PPD + PPD | 12.0 |
| 7 | CaP-PPD + TuMP | 20.6 |
| 8 | CaP-PPD + PPD + TuMP | 19.1 |
| 9 | CaP-PPD-Bx | 187.5 |
| 10 | CaP-PPD-Bx + PPD | 231.9 |
| 11 | CaP-PPD-Bx + TuMP | 263.0 |
| 12 | CaP-PPD-Bx + PPD + TuMP | 268.3 |
| 13 | LPS (10 ng/mL) | 12.4 |
| 14 | LPS (100 ng/mL) | 26.0 |
| 15 | LPS (1000 ng/mL) | 50.9 |

INDUSTRIAL APPLICABILITY

By using the immunoadjuvant of the present invention, antigen-presenting cells can be induced to release a large amount of GM-CSF in a degree comparable to or exceeding that obtainable by stimulating antigen-presenting cells with LPS which is known to have a potent immunostimulating action. Therefore, it is possible to potently activate antigen-presenting cells for which GM-CSF is acting as an autocline cell growth factor, and to maintain that activated state. Accordingly, by administering the immunoadjuvant of the present invention together with an antigen to a living body of a mammal including human, a humoral immune response and/or cell-mediated immune response to the antigen depending on the activated antigen-presenting cells can be induced, and it becomes possible to perform a vaccine therapy extremely effective to an infectious disease or tumor.

What is claimed is:

1. An immunoadjuvant comprising one kind or two or more kinds of immunostimulating substances carried by each of two or more kinds of different microparticle immunostimulating substance carriers, which at least comprises a combination of (a) microparticle calcium phosphate having a size phagocytizable by cells, and (b) a precipitate of a soluble protein and a mucopolysaccharide formed by coacervation as said microparticle immunostimulating substance carriers, wherein the microparticle calcium phosphate of (a) is microparticle calcium phosphate having a Ca/P molar ratio of 1.3 or higher, containing 1 to 15% by weight of carbonate groups $CO_3^{2-}$, and having a degree of crystallinity, in an XRD spectrum obtained with a CuKα ray, not lower than a degree of crystallinity defined by appearance of broad peaks having centers at 2θ values of 26°, 32° and 34° and appearance of a shoulder with a Miller index of 300 at 33°, and not higher than a degree of crystallinity defined by appearance of peaks or shoulders having centers at 26°, 28.1°, 29°, 32°, 33° and 34° and by separation of peaks with Miller indexes of 211 and 112.

2. The immunoadjuvant according to claim 1, wherein the microparticle calcium phosphate of (a) is calcium phosphate having a maximum diameter of 1 µm or smaller.

3. The immunoadjuvant according to claim 1, wherein the soluble protein in (b) is albumin.

4. The immunoadjuvant according to claim 1, wherein the mucopolysaccharide in (b) is heparin.

5. The immunoadjuvant according to claim 1, wherein the precipitates of a soluble protein and a mucopolysaccharide formed by coacervation of (b) are precipitates crosslinked by using an inter-protein molecule crosslinking agent.

6. The immunoadjuvant according to claim 1, wherein the immunostimulating substance consists of one kind or two or more kinds of inducers of a substance selected from the group consisting of cytokines, chemokines, cell growth factors, and hormones.

7. The immunoadjuvant according to claim 1, wherein the immunostimulating substance consists of one kind or two or more kinds of substances selected from the group consisting of tuberculin, tuberculin purified protein derivative (PPD), soluble ingredients originating in microorganisms, trehalose 6,6'-dimycolate, lipopolysaceharides, lipid A, oligonucleotides, β-glucans, keyhole limpet hemocyanin, muramyl dipeptide, bestatin, levamisole, cytokines, chemokines, cell growth factors, and hormones.

8. The immunoadjuvant according to claim 7, wherein the soluble ingredients originating in microorganisms consist of one kind or two or more kinds of extracts selected from the group consisting of alcohol extracts, acetone extracts, pyridine extracts and hot water extracts of microorganisms.

9. The immunoadjuvant according to claim 7, wherein the microorganisms are bacteria.

10. The adjuvant according to claim 1, which is for internal administration to a mammal including human together with an antigen to induce a systemic immune response to the antigen.

11. The immunoadjuvant according to claim 10, wherein the antigen consists of one kind or two or more kinds of substances selected from the group consisting of fungi, Actinomycetes, bacteria, viruses, phages, rickettsias, protozoans, ingredients of fungi, ingredients of Actinomycetes, ingredients of bacteria, ingredients of viruses, ingredients of phages, ingredients of rickettsias, ingredients of protozoans, tumor tissues, tumor cells, tumor cell ingredients, tumor antigen proteins, and tumor antigen peptides.

12. The immunoadjuvant according to claim 1, which is for administration into a tumor tissue of a mammal including human denatured by a physical means to induce an antitumor immune response.

13. The immunoadjuvant according to claim 12, wherein the physical means consists of one kind or two or more kinds of means selected from the group consisting of microwave irradiation, radiofrequency ablation, cryoablation, electrotome heating, hot water injection, alcohol injection, embolization, radiation exposure, laser beam irradiation and sonic disruption.

14. The immunoadjuvant according to claim 1, which is for administration to a mammal including human after externally mixed with immunocompetent cells to induce a systemic immune response in the living body of the mammal.

15. The immunoadjuvant according to claim 14, wherein the immunocompetent cells consists of one kind or two or more kinds of cells selected from the group consisting of dendritic cells, macrophages, B lymphocytes, T lymphocytes, natural killer cells, natural killer T cells, and hematopoietic stem cells.

16. A vaccine containing the immunoadjuvant according to claim 1 and an antigen.

* * * * *